United States Patent
Landham et al.

(12) 
(10) Patent No.: US 6,436,439 B1
(45) Date of Patent: Aug. 20, 2002

(54) GEL FORMULATION

(75) Inventors: Rowena Roshanthi Landham, Sittingbourne; Rupert Heinrich Sohm, Tonbridge, both of (GB)

(73) Assignee: Syngenta Limited, Surrey (GB)

(*) Notice: Subject to any disclaimer, the term of this patent is extended or adjusted under 35 U.S.C. 154(b) by 0 days.

(21) Appl. No.: 08/509,067

(22) Filed: Jul. 31, 1995

(30) Foreign Application Priority Data

Aug. 3, 1994 (GB) .............................................. 9415690
May 11, 1995 (GB) .............................................. 9509559

(51) Int. Cl.$^7$ ......................... A01N 25/04; A61K 9/10; A61K 47/02
(52) U.S. Cl. ......................... 424/484; 516/111; 424/405
(58) Field of Search .................. 424/405, 421, 424/484, 489; 71/64.09, DIG. 1; 106/812; 516/100–111

(56) References Cited

U.S. PATENT DOCUMENTS

| | | | |
|---|---|---|---|
| 3,030,266 A | 4/1962 | Cuille et al. | |
| 3,767,787 A | 10/1973 | Segal | 424/76 |
| 4,698,362 A | 10/1987 | Shafer | 514/490 |
| 5,080,226 A | 1/1992 | Hodakowski et al. | 206/205 |
| 5,139,152 A | 8/1992 | Hodakowski et al. | 206/524.7 |
| 5,222,595 A | 6/1993 | Gouge et al. | 206/205 |
| 5,224,601 A | 7/1993 | Gouge et al. | 206/524.7 |
| 5,248,038 A | 9/1993 | Hodakowski et al. | 206/524.7 |
| 5,253,759 A | 10/1993 | Gouge et al. | 206/524.7 |
| 5,279,421 A | 1/1994 | Gouge et al. | 206/484 |
| 5,280,835 A | 1/1994 | Edwards et al. | 206/484 |
| 5,346,068 A | 9/1994 | Gouge et al. | 206/524.7 |
| 5,395,616 A | 3/1995 | Edwards et al. | 424/405 |
| 5,395,617 A | 3/1995 | Edwards et al. | 424/405 |
| 5,403,589 A | 4/1995 | Edwards et al. | 424/405 |
| 5,407,680 A | 4/1995 | Edwards et al. | 424/405 |
| 5,419,909 A | 5/1995 | Edwards et al. | 424/405 |
| 5,427,794 A | 6/1995 | Miles | 424/405 |
| 5,439,683 A | 8/1995 | Hodakowski et al. | 424/408 |

FOREIGN PATENT DOCUMENTS

| | | |
|---|---|---|
| AU | 73856/91 | 10/1991 |
| DE | 4304831 | 1/1994 |
| EP | 62453 | 10/1982 |
| EP | 131735 | 1/1985 |
| EP | 251464 | 1/1988 |
| EP | 518689 | 12/1992 |
| GB | 1395502 | 5/1975 |
| GB | 2067407 | 7/1981 |
| JP | 54/92630 | 7/1979 |
| JP | 57/139005 | 8/1982 |
| JP | 62/192301 | 8/1987 |
| JP | 62/201803 | 9/1987 |
| WO | WO92/1374 | 2/1992 |
| WO | WO92/1375 | 2/1992 |
| WO | WO92/1376 | 2/1992 |
| WO | WO92/1378 | 2/1992 |
| WO | WO92/17385 | 10/1992 |

OTHER PUBLICATIONS

Somasundaran et al., *Colloids & Surfaces* 63, 49 (19920).
Degussa Technical Bulletin—*Aerosil® as a Thickening Agent for Liquid Systems.*
Degussa Technical Bulletin—*Aerosil® in Pharmaceuticals and Cosmetics.*

*Primary Examiner*—Edward J. Webman

(57) ABSTRACT

The present invention provides a gel formulation comprising the components: a. an agrochemical (such as a herbicide, insecticide, fungicide, adjuvant, synergist or penetrant); b. an inorganic particulate filler (such a flame hydrolysed silica) having a surface area in the range 10 to 400 m$^2$/g, the surface of said filler having hydrophilic characteristics; c. an activator having a polar group capable of interacting with component b to produce a gel; and optionally, d. a diluent.

20 Claims, No Drawings

GEL FORMULATION

The present invention relates to a gel formulation, said formulation being water dispersible and being especially useful for formulating agrochemicals.

A formulation comprising a hazardous material, a surfactant and a gelling agent is disclosed in U.S. Pat. No. 5,139,152. Although it is desirable to prepare formulations at ambient temperature, all the Examples of U.S. Pat. No. 5,139,152 concern formulations prepared at elevated temperatures. EP-A-0347222 discloses a liquid in an envelope of water-soluble or water-dispersible material.

The present invention provides a gel formulation comprising the components: a. an agrochemical; b. an inorganic particulate filler having a surface area in the range 10 to 400 $m^2/g$, the surface of said filler having hydrophilic characteristics; c. an activator having a polar group capable of interacting with component b to produce a gel; and optionally, d. a diluent. The use of an inorganic particulate filler allows the gel formulation to disperse well if it is mixed with water.

The formulation of the present invention is suitable for containment in a sachet of water-soluble or water dispersible material.

Polar groups are, for example, nonionic hydroxy or alkoxy (such as alkyleneoxy, particularly ethyleneoxy or propyleneoxy) groups.

In one aspect the activator is a compound of formula $R(O(CHR^4)_p)_nX$ wherein p is an integer from 2 to 4; n is 0 or an integer from 1 to 200; $R^4$ is hydrogen or methyl; R is hydrogen, alkyl, alkenyl, alkynyl, phenyl (optionally substituted by alkyl, alkenyl, alkynyl, phenylalkenyl, phenylalkynyl or phenylalkyl), a sugar residue or a natural product (such as a lignin or cellulose); wherein the foregoing R groups are optionally substituted with $CO_2R^1$, $O_2CR^1$ or $NR^1R^2$; X is hydrogen, hydroxy, alkyl, alkoxy, alkenyl, alkynyl, phenyl, $CO_2T^1$ or $NR^1R^2$; the aliphatic and aromatic groups of X are optionally substituted with $CO_2R^1$, $O_2CR^1$, $NH_2$, $NHR^1$ or $NR^1R^2$; $R^1$ and $R^2$ are independently alkyl, phenyl or phenylalkyl; and, $T^1$ is hydrogen or an alkali metal; or R is a substituted siloxylalkylenyl group.

For a compound of formula $R(O(CHR^4)_p)_nX$ the $CHR^4$ groups are the same or different and the $O(CHR^4)_p$ groups are the same or different. The compound of formula $R(O(CHR^4)_p)_nX$ can, alternatively, be presented as R—G—X, wherein R and X are as defined above, and G is 1–200 alkyleneyloxy groups independently selected from the group comprising: $OCH_2CH_2$, $OCH_2CH(CH_3)$ and $OCH(CH_3)CH_2$. Thus, said compound is, for example, $R(OCH_2CH_2)_5(OCH(CH_3)CH_2)_{30}(OCH_2CH_2)_5X$, $R(OCH_2CH_2)_{13}X$ or $R(OCH_2CH(CH_3))_{13}(OCH_2CH_2)_{26}X$.

In another, and much preferred, aspect the $(CHR^4)$ groups are independently selected from the group comprising: $CH_2CH_2$, $CH_2CH(CH_3)$ and $CH(CH_3)CH_2$.

In yet another aspect the activator is a compound of formula $R(O(CHR^4)_p)_nX$ wherein the $(CHR^4)$ groups are independently selected from the group comprising: $CH_2CH_2$, $CH_2CH(CH_3)$ and $CH(CH_3)CH_2$; n is 0 or an integer from 1 to 200; R is hydrogen, alkyl, alkenyl, alkynyl, phenyl (optionally substituted by alkyl, alkenyl, alkynyl, phenylalkenyl, phenylalkynyl or phenylalkyl), a sugar residue or a natural product (such as a lignin or cellulose); wherein the foregoing R groups are optionally substituted with $CO_2R^1$, $O_2CR^1$ or $NR^1R^2$; X is hydrogen, hydroxy, alkyl, alkoxy, alkenyl, alkynyl, phenyl, $CO_2T^1$ or $NR^1R^2$; the aliphatic and aromatic groups of X are optionally substituted with $CO_2R^1$, $O_2CR^1$, $NH_2$, $NHR^1$ or $NR^1R^2$; $R^1$ and $R^2$ are independently alkyl, phenyl or phenylalkyl; and, $T^1$ is hydrogen or an alkali metal; or R is a substituted siloxylalkylenyl group. (Thus, said compound is, for example, $R(OCH_2CH_2)_5(OCH(CH_3)CH_2)_{30}(OCH_2CH_2)_5X$, $R(OCH_2CH_2)_{13}X$ or $R(OCH_2CH(CH_3))_{13}(OCH_2CH_2)_{26}X$.)

In a further aspect the activator is a compound of formula $R(O(CHR^4)_p)_nOH$, wherein the $CHR^4$ groups are the same or different and the $O(CHR^4)_p$ groups are the same or different, and wherein R is hydrogen, $C_{8-24}$ alkyl, $C_{8-24}$ alkenyl, $C_{8-24}$ alkynyl or phenyl (optionally substituted by alkyl, alkenyl, alkynyl, phenyl($C_{2-4}$)alkenyl, phenyl($C_{2-4}$)alkynyl or phenyl($C_{1-4}$)alkyl); $R^4$ is hydrogen or methyl; p is an integer from 2 to 4; and n is 0 or an integer from 1 to 50.

In a still further aspect the activator is a compound of formula $R(O(CHR^4)_p)_nOH$ wherein p is 2.

In another aspect the activator is a compound of formula $R(O(CHR^4)_p)_nOH$ wherein n is an integer in the range 10 to 50.

It is preferred that R is alkyl, alkenyl, or phenyl (optionally substituted by phenyl($C_{2-4}$)alkenyl or phenyl($C_{1-4}$)alkyl).

In a further aspect the activator is a compound of formula $HO(CH_2CHOR^5)_mH$, wherein m is an integer from 1 to 30; $R^5$ is hydrogen or $COR^6$; and $R^6$ is $C_{1-4}$ alkyl.

An activator having a polar group capable of interacting with component b. includes a cationic surfactant, especially a compound of formula $R^9R^{10}R^{11}R^{12}N^+Y^-$, wherein $R^9$, $R^{10}$, $R^{11}$ and $R^{12}$ are, independently, alkyl, and $Y^-$ is a suitable anion (such as chloride, bromide or iodide).

Alkyl groups preferably contain, unless stated otherwise, from 1 to 24, especially from 1 to 6, for example from 1 to 4, carbon atoms in straight or branched chain form. Alkyl is, for example, methyl, ethyl, n-propyl, iso-propyl or n-butyl.

Alkenyl and alkynyl groups preferably contain from 6 to 24, especially from 10 to 20, carbon atoms in straight or branched chain form. Alkenyl is, for example, linolenyl, linolyl, licosenoyl, erucyl, palmitolyl, oleyl or undecenyl.

An alkali metal is, for example, sodium or potassium.

Substituted siloxylalkylenyl includes $(R^7SiO)_2R^8Si(CH_2)_qO(CHR^4)_pX$, wherein the $(CHR_4)_p$ and X moieties are as defined above, $R^7$ and $R^8$ are independently $C_{1-6}$ alkyl and q is an integer from 1 to 10.

A sugar residue is preferably a furanoside or pyranoside (such as sorbose, sorbitose, glucose, fructose or mannose) in which the 6-hydroxy group has been esterified with a long-chain fatty acid (such as lauric, stearic, oleic, palmitic, sesquioleic or octadecenoic acid) and optionally one or more of the sugar's other hydroxy groups is replaced by G-X, wherein X is as defined above, and G is 1–200 oxyalkylenyl groups independently selected from the group comprising: $OCH_2CH_2$, $OCH_2CH(CH_3)$ and $OCH(CH_3)CH_2$.

Alkylenyl is an alkyl chain comprising one or more methylene (ie $CH_2$) groups. The alkylenyl chain is optionally substituted with methyl.

Activators of formula $R(O(CHR^4)_p)_nX$ are, for example, sold under the tradenames PLURONIC (from BASF) or SYNPERONIC PE (from ICI). Activators of formula $R(O(CHR^4)_p)_nX$ include SOPROPHOR BSU, SYNPERONIC NP15, SYNPERONIC A4, SYNPERONIC NPE 1800, BRIJ 96, SOPROPHOR S25, SOPROPHOR S40, PEG 400, SPAN 20, SPAN 40, SPAN 60, SPAN 65, SPAN 80, SPAN 83 and SPAN 85, ATLOX 4848 and 4849 and TENSIOFIX HVO 90. Activators of formula $R^9R^{10}R^{11}R^{12}N^+Y^-$ include ARQUAD 16/50.

The word agrochemical includes an active ingredient such as a herbicide {such as a benzo-2,1,3-thiadiazin-4-one-2,2-dioxide (for example bentazone), a hormone herbicide (for example a phenoxy alkanoic acid such as MCPA, MCPA-thioethyl, dichlorprop, 2,4,5-T, MCPB, 2,4-D, 2,4-DB, mecoprop, trichlopyr, fluroxypyr or clopyralid or a derivative thereof (for example a salt, ester or amide thereof)), a 1,3 dimethylpyrazole derivative (for example pyrazoxyfen, pyrazolate or benzofenap), a dinitrophenol or a derivative thereof (for example dinoterb, dinoseb or its ester or dinoseb acetate), a dinitroaniline (for example dinitramine, trifluralin, ethalflurolin, pendimethalin or oryzalin), an arylurea (such as diuron, flumeturon, metoxuron, neburon, isoproturon, chlorotoluron, chloroxuron, linuron, monolinuron, chlorbromuron, daimuron or methabenzthiazuron), a phenylcarbamoyloxyphenyl-carbamate (such as phenmedipham or desmedipham), a 2-phenylpyridazin-3-one (such as chloridazon or norflurazon), a uracil (such as lenacil, bromacil or terbacil), a triazine (such as atrazine, simazine, aziprotryne, cyanazine, prometryn, dimethametryn, simetryne or terbutryn), a phosphorothioate (such as piperophos, bensulide or butamifos), a thiocarbamate (such as prosulfocarb, cycloate, vernolate, molinate, thiobencarb, butylate, EPTC, tri-allate, di-allate, esprocarb, tiocarbazil, pyridate or dimepiperate), a 1,2,4-triazin-5-one (such as metamitron or metribuzin), a benzoic acid (such as 2,3,6-TBA, dicamba or chloramben), an anilide (such as pretilachlor, butachlor, alachlor, propachlor, propanil, metazachlor, metolachlor, acetochlor or dimethachlor), a dihalobenzonitrile (such as dichlobenil, bromoxynil or ioxynil), a haloalkanoic herbicide (such as dalapon, TCA or a salt thereof), a diphenylether (such as lactofen, fluroglycofen or a salt or ester thereof, nitrofen, bifenox, aciflurofen or a salt or ester thereof, oxyfluorfen, fomesafen, chlornitrofen or chlomethoxyfen), an aryloxyphenoxypropionate (such as diclofop or an ester thereof (such as the methyl ester), fluazifop or an ester thereof, haloxyfop or an ester thereof, quizalofop or an ester thereof or fenoxaprop or an ester thereof (such as the ethyl ester), a cyclohexanedione (such as alloxydim or a salt thereof, sethoxydim, cycloxydim, tralkoxydim or clethodim), a sulfonyl urea (such as chlorsulfuron, sulfometuron, metsulfuron or an ester thereof, bensulfuron or an ester thereof (such as DPX-M6313), chlorimuron or an ester (such as the ethyl ester) thereof, pirimisulfuron or an ester (such as the methyl ester) thereof, 2-[3-(4-methoxy-6-methyl-1,3,5-triazinyl)-3-methylureidosulphonyl)benzoic acid or an ester (such as the methyl ester) thereof, (DPX-L5300) or pyrazosulfuron), an imidazolidinone herbicide (such as imazaquin, imazamethabenz, imazapyr or imazethapyr), an arylanilide herbicide (such as flamprop or an ester thereof, benzoylprop-ethyl or diflufenican), an amino acid herbicide (such as glyphosate or glufosinate or a salt or ester thereof, sulphosate or bialaphos), an organoarsenical herbicide (such as monosodium methanearsonate (MSMA)), a herbicidal amide derivative (such as napropamide, propyzamide, carbetamide, tebutam, bromobutide, isoxaben, naproanilide or naptalam), a herbicidal triketone (such as sulcotrione), a miscellaneous herbicide (such as ethofumesate, cinmethylin, difenzoquat or a salt thereof such as the methyl sulphate salt, clomazone, oxadiazon, bromofenoxim, barban, tridiphane, flurochloridone, quinclorac, dithiopyr or mefanacet) or a contact herbicide (such as a bipyridylium herbicide for example a herbicide in which the active entity is paraquat or diquat)}, an insecticide {such as a pyrethroid (such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin or 5-benzyl-3-furylmethyl-(E)-(1R, 3S)-2,2-dimethyl-3-(2-oxothiolin-3-ylidenemethyl) cyclopropane carboxylate), an organophosphate (such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, terbufos, fensulfothion, fonofos, phorate, phoxim, pyrimiphos-methyl, pyrimiphos-ethyl, fenitrothion or diazinon), an insecticidal carbamates (such as pirimicarb, cloethocarb, carbofuran, furathiocarb, ethiofencarb, aldicarb, thiofurox, carbosulfan, bendiocarb, fenobucarb, propoxur or oxamyl), a benzoyl urea (such as triflumuron, or chlorfluazuron), an organic tin compound (such as cyhexatin, fenbutatin oxide or azocyclotin), an insecticidal macrolide (such as an avermectin or milbemycin, for example abamectin, ivermectin, or milbemycin), an insecticidal hormone or pheromone, an organochlorine compound (such as benzene hexachloride, DDT, chlordane or dieldrin), an insecticidal amidine (such as chlordimeform or amitraz), imidacloprid, cartap, buprofezin, chlofentezine, flubenzimine, hexythiazox, tetradifon, a motilicide (such as dicofol or propargite), an acaricides (such as bromopropylate, chlorobenzilate) or an insect growth regulator (such as hydramethylron, cyromazine, methoprene, chlorofluazuron or diflubenzuron)}, a fungicide {such as (RS)-1-aminopropylphosphonic acid, (RS)-4-(4-chlorophenyl)-2-phenyl-2-(1H-1,2,4-triazol-1-ylmethyl) butyronitrile, (Z)-N-but-2-enyloxymethyl-2-chloro-2',6'-diethylacetanilide, 1-(2-cyano-2-methoxyiminoacetyl)-3-ethyl urea, 4-(2,2-difluoro-1,3-benzodioxol-4-yl)pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-[N-(3-chloro-2,6-xylyl)-2-methoxyacetamido]-g-butyrolactone, N-(2-methoxy-5-pyridyl)-cyclopropane carboxamide, alanycarb, aldimorph, ampropylfos, anilazine, azaconazole, BAS 490F, benalaxyl, benomyl, biloxazol, binapacryl, bitertanol, blasticidin S, bromuconazole, bupirimate, butenachlor, buthiobate, captafol, captan, carbendazim, carbendazim chlorhydrate, carboxin, chinomethionate, chlorbenzthiazone, chloroneb, chlorothalonil, chlorozolinate, clozylacon, copper containing compounds such as copper oxychloride, copper oxyquinolate, copper sulphate, copper tallate, and Bordeaux mixture, cycloheximide, cymoxanil, cyproconazole, cyprodinyl, cyprofuram, debacarb, di-2-pyridyl disulphide 1,1'-dioxide, dichlofluanid, dichlone, diclobutrazol, diclomezine, dicloran, didecyl dimethyl ammonium chloride, diethofencarb, difenoconazole, 0,0-di-iso-propyl-S-benzyl thiophosphate, dimefluazole, dimetconazole, dimethomorph, dimethirimol, diniconazole, dinocap, dipyrithione, ditalimfos, dithianon, dodemorph, dodine, doguadine, edifenphos, epoxiconazole, etaconazole, ethirimol, ethoxyquin, ethyl (Z)-N-benzyl-N-([methyl (methylthioethylideneamino-oxycarbonyl)amino]thio)-β-alaninate, etridiazole, fenaminosulph, fenapanil, fenarimol, fenbuconazole, fenfuram, fenpiclonil, fenpropidin, fenpropimorph, fentin acetate, fentin hydroxide, ferbam, ferimzone, fluazinam, fludioxonil, fluoroimide, fluquinconazole, flusilazole, flutolanil, flutriafol, folpet, fuberidazole, furametpyr, furalaxyl, furconazole-cis, guazatine, hexaconazole, hydroxyisoxazole, hymexazole, ICIA5504, imazalil, imibenconazole, ipconazole, iprobenfos, iprodione, isopropanyl butyl carbamate, isoprothiolane, kasugamycin, mancozeb, maneb, mepanipyrim, mepronil, metalaxyl, metconazole, methfuroxam, metiram, metiram-zinc, metsulfovax, myclobutanil, NTN0301, neoasozin, nickel dimethyldithiocarbamate, nitrothal-isopropyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyrimethanil, pyroquilon, pyroxyfur, pyrrolnitrin, quaternary ammonium compounds, quinconazole, quinomethionate, quintozene, rabenazole, sodium pentachlorophenate, streptomycin, sulphur, tebuconazole, techlofthalam, tecnazene, tetraconazole, thiabendazole, thicyofen, thifluzamide, 2-(thiocyanomethylthio)benzothiazole, thiophanate-methyl, thiram, timibenconazole, tolclofos-methyl, tolylfluanid, triacetate salt of 1,1'-iminodi(octamethylene)-diguanidine, triadimefon, triadimenol, triazbutyl, triazoxide, tricyclazole, tridemorph, triforine, triflumizole, triticonazole, validamycin A, vapam, vinclozolin, XRD-563, zineb or ziram} or a plant growth regulator {such as abscisic acid, dikegulac, fenpentezol, paclobutrazol, or a gibberellins (for example GA3, GA4 or GA7)}. The word agrochemical includes an adjuvant, synergist or penetrating agent.

Thus, in a further aspect the present invention provides a gel formulation comprising the components: a. a fungicide, herbicide, insecticide, adjuvant, synergist or penetrating agent; b. an inorganic particulate filler having a surface area in the range 10 to 400 m²/g, the surface of said filler having hydrophilic characteristics; c. an activator having a polar group capable of interacting with component b to produce a gel; and optionally, d. a diluent.

It is preferred that the inorganic particulate filler has active sites (especially isolated hydroxy groups) capable of hydrogen bonding with the activator. It is preferred that the inorganic particulate filler is, for example, a silica, preferably flame hydrolysed silica (that is fumed silica).

It is preferred that the inorganic particulate filler has a surface area in the range 100 to 400, particularly 100 to 350, especially 150 to 300 m²/g.

The diluent is preferably a vegetable oil or derivative thereof (such as methyl oleate, soya bean oil, coconut oil or sunflower seed oil), a hydrocarbon (for example SOLVESSO 150 or 200) or derivative thereof (for example cyclohexanone), a chlorinated solvent (such as a chlorinated aromatic, for example chlorotoluene), a paraffinic oil (such as ISOPAR M), a pyrrolidone (such as N-methyl-2-pyrrolidone) or a lactone (such as g-butyrolactone).

In one aspect the present invention provides a gel formulation comprising 1–90% (preferably 10–80%) by weight of an agrochemical, 1–50% (preferably 5–25%) by weight of an activator having a polar group, 1–20% (preferably 2–10% or 1–4%) by weight of an inorganic particulate filler and, optionally 2–80% (preferably 5–50%) by weight of a solvent.

A Bohlin VOR rheometer can be used to measure the elasticity and viscosity of the gel formulation of the present invention under low shear conditions. Here a sinusoidally varying strain (at a frequency of 1 Hz) is applied to a sample of a formulation maintained at 25° C. The resultant stress, which also varies sinusoidally with time, is observed. The ratio of the maximum stress to the maximum strain is known as the complex modulus (G*). By using phase angle shift, δ, between the stress and strain wave forms the complex modulus may be split into two components—the storage (elastic) modulus (G') and the loss (viscous) modulus (G"). The storage and loss moduli are a measure of the energy stored and the energy lost respectively, in an oscillatory cycle. The relative magnitude of the loss and storage moduli (G"/G'=Tan δ) provides information on the elasticity of the gel. The lower the value of Tan δ the greater the degree of gelation. Similarly, gels are characterised by their non-Newtonian flow behaviour, exhibiting, for example, yield values and shear thinning. Yield values can be measured using a Haake Rotovisco RV20 under high shear conditions.

In a still further aspect the present invention provides a gel formulation as hereinbefore described having a storage modulus (G') in the range 2–1000 Pa, preferably in the range 10–200 Pa.

In another aspect the present invention provides a gel formulation as hereinbefore described having a tan δ (ratio of loss modulus to storage modulus) of less than 1, preferably less than 0.5, especially less than 0.2. (Rheological measurements are carried out at a temperature of 25° C. Oscillation measurements are carried out within the linear viscoelastic region as determined by strain sweep measurements made at a frequency of 1 Hz (6.28 rad/s)).

Over and above the components already mentioned, a gel formulation of the present invention may also comprise an adhesive, an antifoaming agent, a buffer, a deodorant, a dispersant, a dye, an emetic, an emulsifier, a plasticiser, a preservative, an odourant, a perfume, a safener, a further solvent, a stabiliser, a synergist, a thickener or a wetting agent.

When the gel formulation of the invention is to be contained in a water-soluble or water dispersible sachet it is preferred that a plasticiser is included in the gel. The plasticiser is preferably present in the range 0.1 to 5% (especially 0.3 to 3%, for example 0.3 to 0.75%) by weight. Suitable plasticisers include glycols (for example ethylene glycol) glycerine, water, PEG 200 and dibutylphthalate.

In a further aspect the present invention provides a containerisation system comprising a water-soluble or water dispersible bag containing a gel of the present invention.

The water-soluble or water dispersible bag can be made from a variety of materials and preferred materials are polyethylene oxide, methyl cellulose or, especially, polyvinylalcohol (PVA). The PVA is generally partially or fully alcoholysed or hydrolysed, for example 40–100%, especially 80–100%, alcoholysed or hydrolysed polyvinylacetate film. It is preferred that the PVA film is a laminate of two or more thicknesses of film, a surface modified film or a co-extruded film (such as is described in WO 94/29188).

The water-soluble or water dispersible bag can be formed and filled using standard techniques (such as thermoforming or vertical form-fill-sealing).

In another aspect the containerisation system comprises a bag-in-bag arrangement comprising a water-soluble or water dispersible bag holding a gel of the present invention and a second water-soluble or water dispersible bag also holding a gel of the present invention. This bag-in-bag arrangement can be used, for example, to contain a gel of the present invention comprising a fungicide, herbicide or insecticide in the inner bag and a gel of the present invention comprising adjuvant, synergist or penetrating agent in the outer bag.

In a further aspect the containerisation system provides two water-soluble or water dispersible bags joined at a common seal, one containing a gel of the present invention comprising a fungicide, herbicide or insecticide the other bag containing a gel of the present invention comprising an adjuvant, synergist or penetrating agent.

In another aspect the containerisation system comprises a bag-in-bag arrangement comprising a first water-soluble or water dispersible bag holding a gel of the present invention and a second water-soluble or water dispersible bag holding an agrochemical composition (such as a liquid, granule, powder or gel composition comprising a fungicide, herbicide, insecticide, adjuvant, synergist or penetrating agent).

In a further aspect the containerisation system comprises a bag-in-bag arrangement comprising a first water-soluble or water dispersible bag holding an agrochemical composition (such as a liquid, granule, powder or gel composition comprising a fungicide, herbicide, insecticide, adjuvant, synergist or penetrating agent) and a second water-soluble or water dispersible bag holding a gel of the present invention.

In another aspect the containerisation system provides two water-soluble or water dispersible bags joined at a common seal, one containing a gel of the present invention comprising a fungicide, herbicide, insecticide, adjuvant, synergist or penetrating agent the other bag containing an agrochemical composition (such as a liquid, granule, powder or gel composition comprising a fungicide, herbicide, insecticide, adjuvant, synergist or penetrating agent).

In a still further aspect the containerisation system comprises a bag-in-bag arrangement comprising a first water-soluble or water dispersible bag holding a gel of the present invention and a second water-soluble or water dispersible bag surrounding the first water-soluble or water dispersible bag. The advantage of this system is that the second bag presents a barrier to any matter leaking from the first bag.

In use the containerisation system can be mixed with water to give a sprayable solution or dispersion of the agrochemical.

The gel formulation of the invention can be made simply by mixing all the components of the gel at ambient temperature. In another aspect therefore the present invention provides a process for preparing a gel formulation as defined above.

The following Examples illustrate the invention. SOLVESSO, SOPROPHOR, SYNPERONIC, BRIJ, AEROSIL, ATLOX, RHODAFAC, TURBOCHARGE and TENSIOFIX are trade marks or trade names.

EXAMPLE 1

| Component | Amount (% w/w) |
| --- | --- |
| (A) Fluazifop-P-butyl | 62.5^ |
| (B) Methyl oleate | to 100 |
| (C) Fumed silica powder (surface area 200 m$^2$/g) | 2.5 |
| (D) SOPROPHOR BSU | 12.0 |
| (E) SOPROPHOR FL | 1.5 |
| (F) Ethylene glycol | 0.8 |
| (G) BRIJ 93 | 1.0 |
| (H) BRIJ 96 | 6.0 |

^ Amount of actual active ingredient present.
(A) and (B) were mixed and (C) was blended into the resulting mixture using a high shear mixer. (D), (E), (F), (G) and (H) were then added to the resulting mixture sequentially. The mixture thickened significantly to give a gel that was water dispersible, showed good emulsion stability and had the following rheological characteristics under high shear conditions:
Apparent viscosity (mPa, D 300s$^{-1}$): 304 at 25° C.
Yield value (Pa, Casson): 6.5

EXAMPLE 2

Silica powder (2.5% w/w, fumed silica with a surface area of 200 m$^2$/g) was high shear mixed into an oil based mixture comprising fluazifop-P-butyl (62.5% w/w, amount of actual active ingredient present) and methyl oleate (the make up component). SOPROPHOR BSU (12% w/w) was then blended into the dispersion. Significant thickening of the formulation occurred.

EXAMPLE 3

The procedure for Example 2 was repeated, except that the solvent methyl oleate was replaced by an aromatic organic solvent (SOLVESSO 200). A gel formulation was obtained.

EXAMPLE 4

The procedure for Example 2 was repeated, except that SYNPERONIC NP15 was used in place of SOPROPHOR BSU. A gel formulation was obtained.

EXAMPLE 5

The procedure for Example 2 was repeated, except that SYNPERONIC A4 was used in place of SOPROPHOR BSU. A gel formulation was obtained.

EXAMPLE 6

Silica powder (2.5% w/w, fumed silica with a surface area of 200 m$^2$/g) was high shear mixed into an oil based mixture comprising fluazifop-P-butyl (62.5% w/w, amount of actual active ingredient present) and methyl oleate (the make up component). SOPROPHOR BSU (14% w/w) and BRIJ 96 (3% w/w) were then blended into the dispersion. Significant thickening of the formulation occurred. An anionic emulsifier, dodecylbenzene sulphonic acid amine salt (3% w/w) was then blended into the dispersion. The resultant gel was water dispersible and showed good emulsion stability when diluted in water (5% v/v dilution).

Some of the gel produced (50 g) was packaged in a water soluble sachet formed of polyvinyl alcohol film, overpacked in a polythene bag and stored under ambient conditions.

EXAMPLE 7

Silica powder (2.5% w/w, fumed silica with a surface area of 200 m$^2$/g) was dispersed in fluazifop-P-butyl (62.5% w/w, amount of actual active ingredient present) using a high shear blender. SYNPERONIC A4 (12% w/w), water (the make-up component) and calcium dodecylbenzenesulphonate (70% in n-butanol) (3.5% w/w) were then blended into the dispersion. Significant thickening occurred.

Some of the gel produced (50 g) was packaged in a water soluble sachet formed of polyvinyl alcohol film. After 50 days storage under ambient conditions the sachet showed no sign of leakage or permeation.

EXAMPLE 8

| Component | Amount (% w/w) |
| --- | --- |
| (A) Lambda cyhalothrin | 25.0^ |
| (B) Methyl oleate | to 100 |
| (C) Fumed silica powder (surface area 200 m$^2$/g) | 4.0 |
| (D) SOPROPHOR BSU | 4.2 |
| (E) SYNPERONIC A4 | 0.8 |
| (F) Ethylene glycol | 0.8 |
| (G) RHODAFAC 2283 | 3.2 |

^ Amount of actual active ingredient present.
(A) and (B) were mixed and (C) was blended into the resulting mixture using a high shear mixer. (D), (E), (F) and (G) were then added to the resulting mixture sequentially. The mixture thickened significantly to give a gel that was water dispersible, showed good emulsion stability and had the following rheological characteristics under low shear conditions:
Complex modulus G*: 83 Pa
Elastic modulus G': 81 Pa
Viscous modulus G": 15 Pa
Tan δ: 0.19

EXAMPLE 9

TURBOCHARGE (available from ZENECA Limited; 95% w/w; which comprises nonionic surfactants in a solvent system, the nonionic surfactants having a role as adjuvants and as activators) and silica powder (5% w/w, fumed silica with a surface area of 200 m$^2$/g) were mixed thoroughly using a high shear mixer. A viscous, thixotropic gel with the following rheological characteristics resulted:

Complex modulus G*: 40 Pa

Elastic modulus G': 39 Pa

Viscous modulus G": 12 Pa

Tan δ: 0.31

EXAMPLE 10

| Component | Amount (% w/w) |
|---|---|
| (A) Acetochlor | 75.0^ |
| (B) AEROSIL COK 84 silica | 2.5 |
| (C) Polyethylene glycol (MW 400) | 8.0 |
| (D) SYNPERONIC NPE 1800 | 6.0 |
| (E) Calcium dodecylbenzenesulphonate (70% in n-butanol) | 2.0 |

^ Amount of actual active ingredient present.

(A) and (B) were mixed using a high shear mixer. (C), (D) and (E) were then added to the resulting dispersion and the mixture was high shear mixed. The resulting gel was water dispersible, showed good emulsion stability and had the following (low shear) rheological characteristics:
Complex modulus G*: 82 Pa
Elastic modulus G': 81 Pa
Viscous modulus G": 13 Pa
Tan δ: 0.16

EXAMPLE 11

| Component | Amount (% w/w) |
|---|---|
| (A) Tralkoxydim | 10.0^ |
| (B) ATLOX 4848 | 5.0 |
| (C) ATLOX 4849 | 2.0 |
| (D) Ethylene glycol | 1.0 |
| (E) AEROSIL A200 silica | 2.5 |
| (F) Monochlorotoluene | 50.0 |
| (G) SOLVESSO 150 | to 100 |

^ Amount of actual active ingredient present.

The components were mixed using a high shear blender to produce a gel that was water dispersible, showed good emulsion stability and had the following rheological characteristics:
Complex modulus G*: 30 Pa
Elastic modulus G': 30 Pa
Viscous modulus G": 1.4 Pa
Tan δ: 0.05

EXAMPLE 12

| Component | Amount (% w/w) |
|---|---|
| (A) Hexaconazole | 20.0^ |
| (B) AEROSIL A200 silica | 4.5 |
| (C) SYNPERONIC NP15 | 12.0 |
| (D) Ethylene glycol | 1.0 |
| (E) Calcium dodecylbenzenesulphonate (70% in n-butanol) | 1.0 |
| (F) Cyclohexanone | to 100 |

^ Amount of actual active ingredient present.

The components were mixed using a high shear blender to produce a gel that was water dispersible, showed good emulsion stability and had the following rheological characteristics:
Complex modulus G*: 22 Pa
Elastic modulus G': 22 Pa
Viscous modulus G": 4 Pa
Tan δ: 0.18

EXAMPLE 13

The following Table demonstrates the necessity to have both an activator and a silica present in order to obtain a gelled formulation.

| Formulation | G* (Pa) | G' (Pa) | G" (Pa) | Tan δ |
|---|---|---|---|---|
| A | 0.72 | 0.07 | 0.71 | 9.86 |
| B | 1.03 | 0.41 | 0.95 | 2.29 |
| C | 169 | 168 | 15.7 | 0.09 |

Components in formulation A (% w/w): fluazifop-P-butyl (amount of actual active ingredient present) 62.5; AEROSIL A200 silica 2.5; and methyl oleate to 100.

Components in formulation B (% w/w): fluazifop-P-butyl (amount of actual active ingredient present) 62.5; SOPROPHOR BSU 13.0; and methyl oleate to 100.

Components in formulation C (% w/w): fluazifop-P-butyl (amount of actual active ingredient present) 62.5; AEROSIL A200 silica 2.5; SOPROPHOR BSU 13.0; and methyl oleate to 100.

Formulations A, B and C were prepared by mixing the components using a high shear blender.

EXAMPLE 14

| Component | Amount (% w/w) |
|---|---|
| (A) Fluazifop-P-butyl | 62.5^ |
| (B) AEROSIL A200 silica powder | 2.0 |
| (C) BRIJ 96 | 1.0 |
| (D) SYNPERONIC A4 | 3.0 |
| (E) TENSIOFIX HVO 90 | 5.0 |
| (F) Ethylene glycol | 1.0 |
| (G) SOPROPHOR 4D384 | 1.5 |
| (H) AEROSOL OT-B | 2.5 |
| (I) Methylated canola oil | to 100 |

^ Amount of actual active ingredient present.

(B) was added to a mixture of (A) and (I) and the resulting mixture was high shear mixed until it was free of agglomerates. (C), (D), (E) and (F) were then added and the mixture high shear mixed. Significant thickening of the mixture occurred. Finally (G) and (H) were added and the mixture was high shear mixed until a homogenous gel was obtained. The resulting gel had the following rheological characteristics:
Complex modulus G*: 57 Pa
Elastic modulus G': 56 Pa
Viscous modulus G": 9.8 Pa
Tan δ: 0.17

EXAMPLE 15

The procedure for Example 2 was repeated, except that ARQUAD 16/50 [cetyl trimethylammonium bromide (50% in isopropyl alcohol)] was used in place of SOPROPHOR BSU. A gel formulation was obtained.

EXAMPLE 16

The procedure for Example 2 was repeated, except that water was used in place of SOPROPHOR BSU. A gel formulation was obtained.

What is claimed is:

1. A containerization system comprising a containerization system contained in a water-soluble or water-dispersible bag; the gel comprising:
    (a) an agrochemical;
    (b) an inorganic particulate filler having a surface area in the range 10 to 400 m²/g, the surface of said filler having active sites which hydrogen bond with component (c);
    (c) an activator having a polar group which interacts with component (b) to produce a gel, provided that the activator is not water; and optionally,
    (d) a diluent.

2. A containerization system comprising a containerization system contained in a water-soluble or water-dispersible bag; the gel comprising:

(a) an agrochemical;

(b) the product obtained by hydrogen bonding between an inorganic particulate filler having a surface area in the range 10 to 400 m$^2$/g and an activator having a polar group which interacts with said filler to produce a gel, provided that the activator is not water, the surface of said filler having active sites which hydrogen bond with said activator; and optionally, (c) a diluent.

3. A containerization system as claimed in claim 1 wherein the inorganic particulate filler is flame hydrolysed silica.

4. A containerization system as claimed in claim 1 wherein the surface area of the inorganic particulate filler is in the range 100 to 400 m$^2$/g.

5. A containerization system as claimed in claim 1 wherein the activator is a compound of formula R(O(CHR$^4$)$_p$)$_n$X wherein p is an integer from 2 to 4; n is 0 or an integer from 1 to 200; R$^4$ is hydrogen or methyl; R is hydrogen, alkyl, alkenyl, alkynyl, phenyl (optionally substituted by alkyl, alkenyl, alkynyl, phenylalkenyl, phenylalkynyl or phenylalkyl), a sugar residue or a natural product; wherein the foregoing R groups are optionally substituted with CO$_2$R$^1$, O$_2$CR$^1$ or NR$^1$R$^2$; X is hydrogen, hydroxy, alkyl, alkoxy, alkenyl, alkynyl, phenyl, CO$_2$T$^1$ or NR$^1$R$^2$; the aliphatic and aromatic groups of X are optionally substituted with CO$_2$R$^1$, O$_2$CR$^1$, NH$_2$, NHR$^1$ or NR$^1$R$^2$; R$^1$ and R$^2$ are independently alkyl, phenyl or phenylalkyl; and, T$^1$ is hydrogen or an alkali metal; or R is a substituted siloxylalkylenyl group.

6. A containerization system as claimed in claim 1 wherein the activator is a compound of formula R(O(CHR$^4$)$_p$)$_n$OH, wherein the CHR$^4$ groups are the same or different and the O(CHR$^4$)$_p$ groups are the same or different, and wherein R is hydrogen, C$_{8-24}$ alkyl, C$_{8-24}$ alkenyl, C$_{8-24}$ alkynyl or phenyl (optionally substituted by alkyl, alkenyl, alkynyl, phenyl(C$_{2-4}$)alkenyl, phenyl (C$_{2-4}$)alkynyl or phenyl(C$_{1-4}$)alkyl); R$^4$ is hydrogen or methyl; p is an integer from 2 to 4; and n is 0 or an integer from 1 to 50.

7. A containerization system as claimed in claim 1 wherein the activator is a compound of formula R—G—X, wherein R is hydrogen, alkyl, alkenyl, alkynyl, phenyl (optionally substituted by alkyl, alkenyl, alkynyl, phenylalkenyl, phenylalkynyl or phenylalkyl), a sugar residue or a natural product; wherein the foregoing R groups are optionally substituted with CO$_2$R$^1$, O$_2$CR$^1$ or NR$^1$R$^2$; X is hydrogen, hydroxy, alkyl, alkoxy, alkenyl, alkynyl, phenyl, CO$_2$T$^1$ or NR$^1$R$^2$; the aliphatic and aromatic groups of X are optionally substituted with CO$_2$R$^1$, O$_2$CR$^1$, NH$_2$, NHR$^1$ or NR$^1$R$^2$; R$^1$ and R$^2$ are independently alkyl, phenyl or phenylalkyl; T$^1$ is hydrogen or an alkali metal; or R is a substituted siloxylalkylenyl group; and G is 1–200 alkyleneyloxy groups independently selected from the group comprising: OCH$_2$CH$_2$, OCH$_2$CH(CH$_3$) and OCH(CH$_3$)CH$_2$.

8. A containerization system as claimed in claim 1 wherein the activator is a compound of formula R$^9$R$^{10}$R$^{11}$R$^{12}$N$^+$Y$^-$, wherein R$^9$, R$^{10}$, R$^{11}$ and R$^{12}$ are, independently, alkyl, and Y$^-$ is a suitable anion.

9. A containerization system as claimed in claim 1 wherein the agrochemical is a fungicide, herbicide, insecticide, adjuvant, synergist or penetrating agent.

10. A containerisation system providing two water-soluble or water dispersible bags joined at a common seal, one bag containing a gel formulation as claimed in claim 1 which comprises a fungicide, herbicide or insecticide the other bag containing a gel as claimed in claim 1 which comprises an adjuvant, synergist or penetrating agent.

11. A containerization system as claimed in claim 2 wherein the inorganic particulate filler is flame hydrolysed silica.

12. A containerization system as claimed in claim 2 wherein the surface area of the inorganic particulate filler is in the range 100 to 400 m$^2$/g.

13. A containerization system as claimed in claim 2 wherein the activator is a compound of formula R(O(CHR$^4$)$_p$)$_n$X wherein p is an integer from 2 to 4; n is 0 or an integer from 1 to 200; R$^4$ is hydrogen or methyl; R is hydrogen, alkyl, alkenyl, alkynyl, phenyl (optionally substituted by alkyl, alkenyl, alkynyl, phenylalkenyl, phenylalkynyl or phenylalkyl), a sugar residue or a natural product; wherein the foregoing R groups are optionally substituted with CO$_2$R$^1$, O$_2$CR$^1$ or NR$^1$R$^2$; X is hydrogen, hydroxy, alkyl, alkoxy, alkenyl, alkynyl, phenyl, CO$_2$T$^1$ or NR$^1$R$^2$; the aliphatic and aromatic groups of X are optionally substituted with CO$_2$R$^1$, O$_2$CR$^1$, NH$_2$NHR$^1$ or NR$^1$R$^2$; R$^1$ and R$^2$ are independently alkyl, phenyl or phenylalkyl; and T$^1$ is hydrogen or an alkali metal; or R is a substituted siloxylalkylenyl group.

14. A containerization system as claimed in claim 2 wherein the activator is a compound of formula R(O(CHR$^4$)$_p$)$_n$OH, wherein the CHR$^4$ groups are the same or different and the O(CHR$^4$)$_p$ groups are the same or different, and wherein R is hydrogen, C$_{8-24}$ alkyl, C$_{8-24}$ alkenyl, C$_{8-24}$ alkynyl or phenyl (optionally substituted by alkyl, alkenyl, alkynyl, phenyl(C$_{2-4}$)alkenyl, phenyl(C$_{2-4}$)alkynyl or phenyl (C$_{1-4}$)alkyl); R$^4$ is hydrogen or methyl; p is an integer from 2 to 4; and n is 0 or an integer from 1 to 50.

15. A containerization system as claimed in claim 2 wherein the activator is a compound of formula R—G—X, wherein R is hydrogen, alkyl, alkenyl, alkynyl, phenyl (optionally substituted by alkyl, alkenyl, alkynyl, phenylalkenyl, phenylalkynyl or phenylalkyl), a sugar residue or a natural product; wherein the foregoing R groups are optionally substituted with CO$_2$R$^1$, O$_2$CR$^1$ or NR$^1$R$^2$; X is hydrogen, hydroxy, alkyl, alkoxy, alkenyl, alkynyl, phenyl, CO$_2$T$^1$ or NR$^1$R$^2$; the aliphatic and aromatic groups of X are optionally substituted with CO$_2$R$^1$, O$_2$CR$^1$, NH$_2$, NHR$^1$ or NR$^1$R$^2$; R$^1$ and R$^2$ are independently alkyl, phenyl or phenylalkyl; T$^1$ is hydrogen or an alkali metal; or R is a substituted siloxylalkylenyl group; and G is 1–200 alkyleneyloxy groups independently selected from the group comprising: OCH$_2$CH$_2$, OCH$_2$CH(CH$_3$) and OCH(CH$_3$)CH$_2$.

16. A containerization system as claimed in claim 2 wherein the activator is a compound of formula R$^9$R$^{10}$R$^{11}$R$^{12}$N$^+$Y–, wherein R$^9$, R$^{10}$, R$^{11}$ and R$^{12}$ are, independently, alkyl, and Y– is a suitable anion.

17. A containerization system as claimed in claim 2 wherein the agrochemical is a fungicide, herbicide, insecticide, adjuvant, synergist or penetrating agent.

18. A containerization system providing two water-soluble or water dispersible bags joined at a common seal, one bag containing a gel formulation as claimed in claim 14 which comprises a fungicide, herbicide or insecticide the other bag containing a gel formulation as claimed in claim 2 which comprises an adjuvant, synergist or penetrating agent.

19. A containerization system as claimed in claim 4 wherein the surface area of the inorganic particulate filler is in the range 150 to 300 m$^2$/g.

20. A containerization system as claimed in claim 12 wherein the surface area of the inorganic particulate filler is in the range 150 to 300 m$^2$/g.

* * * * *